United States Patent
Okumura et al.

(10) Patent No.: US 9,561,210 B2
(45) Date of Patent: Feb. 7, 2017

(54) THERAPEUTIC AGENT FOR OCULAR DISEASE

(71) Applicant: AskAt Inc., Aichi (JP)

(72) Inventors: Takako Okumura, Aichi (JP); Shinichi Koizumi, Aichi (JP); Hideaki Hara, Gifu (JP)

(73) Assignee: AskAt Inc., Aichi (JP)

( * ) Notice: Subject to any disclaimer, the term of this patent is extended or adjusted under 35 U.S.C. 154(b) by 0 days.

(21) Appl. No.: 14/776,048

(22) PCT Filed: Mar. 31, 2014

(86) PCT No.: PCT/JP2014/059557
§ 371 (c)(1),
(2) Date: Sep. 14, 2015

(87) PCT Pub. No.: WO2014/157727
PCT Pub. Date: Oct. 2, 2014

(65) Prior Publication Data
US 2016/0008317 A1    Jan. 14, 2016

(30) Foreign Application Priority Data

Mar. 29, 2013 (JP) ................. 2013-072979
Jul. 29, 2013 (JP) ................. 2013-156602

(51) Int. Cl.
| | |
|---|---|
| *C07D 311/58* | (2006.01) |
| *A61K 31/352* | (2006.01) |
| *A61K 31/382* | (2006.01) |

(52) U.S. Cl.
CPC ........... *A61K 31/352* (2013.01); *A61K 31/382* (2013.01); *C07D 311/58* (2013.01)

(58) Field of Classification Search
CPC .... C07D 311/58; A61K 31/352; A61K 31/382
See application file for complete search history.

(56) References Cited

U.S. PATENT DOCUMENTS

| 6,034,256 A | 3/2000 | Carter et al. |
| 2005/0049252 A1 | 3/2005 | Carter et al. |

FOREIGN PATENT DOCUMENTS

| JP | 4577534 | 9/2010 |
| WO | 02/05815 | 1/2002 |
| WO | 2005/021004 | 3/2005 |
| WO | 2005/049014 | 6/2005 |
| WO | WO 2005/049014 | * 6/2005 | .......... A61K 31/415 |
| WO | 2013/058303 | 4/2013 | |
| WO | 2014/104414 | 7/2014 | |

OTHER PUBLICATIONS

International Search Report issued May 13, 2014 in International (PCT) Application No. PCT/JP20147/059557.
Obata, "Gankai kara Mita Koenshoyaku-Yokujohen no Shorei kara-", Ginkai, No. 90, 2003, pp. 6-7, ISR.
Yamada, "Ganshikkan to COX-2", Journal of Clinical and Experimental Medicine, vol. 197(2), 2001, pp. 157-158, ISR.
Katori et al., "Cyclooxygenase-2: its rich diversity of roles and possible application of its selective inhibitors", Inflammation Research, vol. 49, 2000, pp. 367-392.
International Preliminary Report on Patentability issued Sep. 29, 2015 in International (PCT) Application No. PCT/JP20147/059557.
Partial English translation of Obata, "Gankai kara Mita Koenshoyaku-Yokujohen no Shorei kara-", Ginkai, No. 90, 2003, pp. 6-7, ISR.
Partial English translation of Yamada, "Ganshikkan to COX-2", Journal of Clinical and Experimental Medicine, vol. 197(2), 2001, pp. 157-158, ISR.
Extended European Search Report issued Sep. 30, 2016 in corresponding European Application No. 14775889.0.

* cited by examiner

*Primary Examiner* — Erich A Leeser
(74) *Attorney, Agent, or Firm* — Wenderoth, Lind & Ponack, L.L.P.

(57) ABSTRACT

The purpose of this invention is to provide a compound for preventing or treating an ocular disease and a pharmaceutical composition comprising the same. This invention provides a pharmaceutical composition comprising a compound as defined by the formula (I') or a pharmaceutically acceptable salt thereof. The pharmaceutical composition is useful for preventing or treating an ocular disease such as retinochoroidal degeneration.

{Chem. 1}

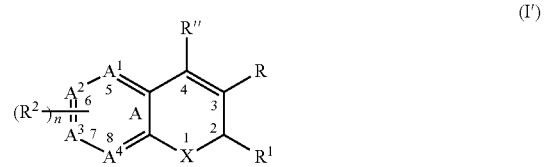

(I')

4 Claims, 1 Drawing Sheet

Scale bar: 100 μm

THERAPEUTIC AGENT FOR OCULAR DISEASE

TECHNICAL FIELD

The present invention relates to a compound as defined by the formula (I) or formula (I') or a pharmaceutically acceptable salt thereof for use in preventing or treating an ocular disease in animal including human. This invention relates to use of the said compound or a pharmaceutically acceptable salt thereof for the manufacture of a medicament for preventing or treating an ocular disease. The invention relates to a method for preventing or treating said diseases comprising administering the said compound or a pharmaceutical composition comprising the same to animal including human. Further, this invention relates to a pharmaceutical composition or a kit comprising the said compound or a pharmaceutically acceptable salt thereof for preventing or treating said diseases.

BACKGROUND ART

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, which limit their therapeutic potential. An alternative to NSAIDs is the use of corticosteroids, which have even more drastic side effects, especially when long term therapy is involved.

NSAIDs prevent the production of prostaglandins by inhibiting enzymes in the human arachidonic acid/prostaglandin pathway. The expression of cyclooxygenase-2 (COX-2) is specifically induced in the pathological conditions such as inflammation, pain, and cancer, and is involved in the generation and maintenance of these conditions. According to the line, a series of drugs called coxibs such as celecoxib, rofecoxib, valdecoxib, parecoxib, and etoricoxib have been developed.

Coxib-drugs are useful for the treatment of diseases mediated by cyclooxygenase-2, such as inflammation, pain, cancer, fever, osteoarthritis, rheumatoid arthritis, migraine, neurodegenerative diseases, cardiovascular disease, osteoporosis, asthma, lupus and psoriasis, dysmenorrhea, premature labor, gout, ankylosing spondylitis, bursitis, heat burn, sprain, and contusion (non-patent literature 1).

The benzopyran, naphtopyran, dihydroquinoline, benzothiopyran and dihydronapthalene derivatives, represented by the formula (I) or formula (I') in this invention are disclosed in the patent literature 1, and preferably selectively inhibit cyclooxygenase-2 over cyclooxygenase-1. Among them, the benzopyran derivative, for example, affords more potent analgesia and more rapid onset of effect than ibuprofen which is the first choice among the conventional drugs. Furthermore it has been confirmed in the preclinical studies that the benzopyran derivatives have lower renal problems which are a matter of concern in conventional COX-2 inhibitors and NSAIDs.

CITATION LIST

Patent Literature

{PL 1} JP Patent No. 4577534

Non-Patent Literature

{NPL 1} Inflamm Res. 2000 August; 49(8):367-92

SUMMARY OF INVENTION

Problems to be Resolved by the Invention

In general, active ingredients involved in coxib-drugs have a sulfonamide group, whereas a compound of formula (I) or a compound of formula (I') is a unique chemical structure, which has neither sulfonamide group nor alkylsulfonyl group but has a carboxylic acid group which may be esterified. Hereafter in the present specification, such coxib-drugs or coxib-compounds, which have neither a sulfonamide group nor an alkylsulfonyl group but have a carboxylic acid group, are called the third generation coxib-drugs or third the generation coxib-compounds. Therefore, the third generation coxib-drugs have a unique pharmacological effects which are never seen in conventional COX-2 inhibitors. In the present invention, a compound represented by a compound of formula (I) may be the same as that of formula (I').

Means of Solving the Problems

When applying the third generation COX-2 inhibitor of the formula (I) or formula (I') to some ocular disease models, the present inventors have surprisingly found that the said inhibitor has an excellent effect against chorioretinal neovascularization. The inventors establish a technical idea that a compound of the present invention is useful for ocular diseases, and have completed the present invention by further examinations.

Namely the present invention discloses:
[1] A compound as defined by the following formula (I') for use in preventing or treating an ocular disease in animal including human, which is referred to as "a compound of the present invention";

{Chem. 1}

(I')

wherein
X is selected from O, S and $NR^a$;
$R^a$ is selected from hydrido; $C_1$-$C_3$-alkyl; (optionally substituted phenyl)-methyl; and phenylmethyl; wherein the phenyl ring is substituted by 1 to 3 substituents independently selected from $C_1$-$C_6$-alkyl, hydroxyl, halo, $C_1$-$C_6$-haloalkyl, nitro, cyano, $C_1$-$C_6$-alkoxy and $C_1$-$C_6$-alkylamino;
R is carboxyl;
R" is selected from hydrido and $C_2$-$C_6$-alkenyl;

$R^1$ is selected from $C_1$-$C_3$-perfluoroalky, chloro, $C_1$-$C_6$-alkylthio, nitro, cyano and cyano-$C_1$-$C_3$-alkyl;

$R^2$ is one or more radicals independently selected from the group consisting of hydrido; halo; $C_1$-$C_6$-alkyl; $C_2$-$C_6$-alkenyl; $C_2$-$C_6$-alkynyl; halo-$C_2$-$C_6$-alkynyl; pheny-$C_1$-$C_6$-alkyl; phenyl-$C_2$-$C_6$-alkynyl; halophenyl-$C_2$-$C_6$-alkynyl; $C_1$-$C_6$-alkoxy-phenyl-$C_2$-$C_6$-alkynyl, phenyl-$C_2$-$C_6$-alkenyl; $C_1$-$C_3$-alkoxy; methylenedioxy; $C_1$-$C_3$-alkoxy-$C_1$-$C_3$-alkyl; $C_1$-$C_3$-alkylthio; $C_1$-$C_3$-alkylsulfinyl; phenyloxy; phenylthio; phenylsulfinyl; $C_1$-$C_3$-haloalkyl-$C_1$-$C_3$-hydroxyalkyl; phenyl-$C_1$-$C_3$-alkoxy-$C_1$-$C_3$-alkyl; $C_1$-$C_3$-haloalkyl; $C_1$-$C_3$-haloalkoxy; $C_1$-$C_3$-haloalkylthio; $C_1$-$C_3$-hydroxyalkyl; $C_1$-$C_3$-hydroxyhaloalkyl; hydroxyimino-$C_1$-$C_3$-alkyl; $C_1$-$C_6$-alkylamino; nitro; cyano; amino; aminosulfonyl; N—($C_1$-$C_6$-alkyl)aminosulfonyl; N-arylaminosulfonyl; N-heteroarylaminosulfonyl; N-(phenyl-$C_1$-$C_6$-alkyl)aminosulfonyl; N-(heteroaryl-$C_1$-$C_6$-alkyl)aminosulfonyl; phenyl-$C_1$-$C_3$-alkylsulfonyl; 5- to 8-membered heterocyclylsulfonyl; $C_1$-$C_6$-alkylsulfonyl; phenyl; optionally substituted phenyl substituted by one or more radials selected from chloro, fluoro, bromo, methoxy, methylthio and methylsulfonyl; 5- to 9-membered heteroaryl; chloro substituted thienyl; phenyl-$C_1$-$C_6$-alkylcarbonyl; phenylcarbonyl; 4-chlorophenylcarbonyl; 4-hydroxyphenylcarbonyl; 4-trifluoromethylphenylcarbonyl; 4-methoxyphenylcarbonyl; aminocarbonyl; formyl; and $C_1$-$C_6$-alkylcarbonyl;

or $R^2$ together with ring A forms a naphthyl, benzofurylphenyl, or quinolyl radical;

the A ring atoms $A^1$, $A^2$, and $A^3$ are carbon and $A^4$ is carbon or nitrogen; n is an integer selected from 1 to 4;

or a pharmaceutically acceptable salt thereof;

[2] A compound described in [1], wherein $R^a$ is selected from hydrido; methyl; ethyl; (4-trifluoromethyl)benzyl; (4-chloromethyl)benzyl; (4-methoxy)benzyl; (4-cyano)benzyl; and (4-nitro)benzyl;

R" is selected from hydrido and ethenyl;

$R^1$ is selected from trifluoromethyl and pentafluoroethyl;

$R^2$ is one or more radicals independently selected from the group consisting of hydrido; chloro; bromo; fluoro; iodo; methyl; tert-butyl; ethenyl; ethynyl; 5-chloro-1-pentynyl; 1-pentynyl; 3,3-dimethyl-1-butynyl; benzyl; phenylethyl; phenylethynyl; 4-chlorophenyl-ethynyl; 4-methoxyphenyl-ethynyl; phenylethenyl; methoxy; methylthio; methylsulfinyl; phenyloxy; phenylthio; phenylsulfinyl; methylenedioxy; benzyloxymethyl; trifluoromethyl; difluoromethyl; pentafluoroethyl; trifluoromethoxy; trifluoromethylthio; hydroxymethyl; hydroxy-trifluoroethyl; methoxymethyl; hydroxyiminomethyl; N-methylamino; nitro; cyano; amino; aminosulfonyl; N-methylaminosulfonyl; N-phenylaminosulfonyl; N-furylaminosulfonyl; N-(benzyl)aminosulfonyl; N-(furylmethyl)aminosulfonyl; benzylsulfonyl; phenylethylaminosulfonyl; furylsulfonyl; methylsulfonyl; phenyl; phenyl substituted with one or more radicals selected from chloro, fluoro, bromo, methoxy, methylthio and methylsulfonyl; benzimidazolyl; furyl; thienyl; thienyl substituted with chloro; benzylcarbonyl; phenylcarbonyl; aminocarbonyl; formyl; and methylcarbonyl;

or a pharmaceutically acceptable salt thereof;

[3] A compound described in [1] or [2], wherein the compound of formula (I') is one or more selected from the group consisting of 6-chloro-2-trifluoromethyl-2H-1-benzopyran-3-carboxylic acid;

6-chloro-7-methyl-2-trifluoromethyl-2H-1-benzopyran-3-carboxylic acid;

8-(1-methylethyl)-2-trifluoromethyl-2H-1-benzopyran-3-carboxylic acid;

6-chloro-7-(1,1-dimethylethyl)-2-trifluoromethyl-2H-1-benzopyran-3-carboxylic acid;

(S)-6-chloro-7-(1,1-dimethylethyl)-2-trifluoromethyl-2H-1-benzopyran-3-carboxylic acid;

6-chloro-8-(1-methylethyl)-2-trifluoromethyl-2H-1-benzopyran-3-carboxylic acid;

2-trifluoromethyl-3H-naphtopyran-3-carboxylic acid;

7-(1,1-dimethylethyl)-2-trifluoromethyl-2H-1-benzopyran-3-carboxylic acid;

6-bromo-2-trifluoromethyl-2H-1-benzopyran-3-carboxylic acid;

8-chloro-2-trifluoromethyl-2H-1-benzopyran-3-carboxylic acid;

6-trifluoromethoxy-2-trifluoromethyl-2H-1-benzopyran-3-carboxylic acid;

(S)-6-trifluoromethoxy-2-trifluoromethyl-2H-1-benzopyran-3-carboxylic acid;

5,7-dichloro-2-trifluoromethyl-2H-1-benzopyran-3-carboxylic acid;

8-phenyl-2-trifluoromethyl-2H-1-benzopyran-3-carboxylic acid;

7,8-dimethyl-2-trifluoromethyl-2H-1-benzopyran-3-carboxylic acid;

6,8-bis(dimethylethyl)-2-trifluoromethyl-2H-1-benzopyran-3-carboxylic acid;

7-(1-methylethyl)-2-trifluoromethyl-2H-1-benzopyran-3-carboxylic acid;

7-phenyl-2-trifluoromethyl-2H-1-benzopyran-3-carboxylic acid;

6-chloro-7-ethyl-2-trifluoromethyl-2H-1-benzopyran-3-carboxylic acid;

6-chloro-8-ethyl-2-trifluoromethyl-2H-1-benzopyran-3-carboxylic acid;

6-chloro-7-phenyl-2-trifluoromethyl-2H-1-benzopyran-3-carboxylic acid;

6,7-dichloro-2-trifluoromethyl-2H-1-benzopyran-3-carboxylic acid;

6,8-dichloro-2-trifluoromethyl-2H-1-benzopyran-3-carboxylic acid;

2-trifluoromethyl-3H-naphtho[2,1-b]pyran-3-carboxylic acid;

6-chloro-8-methyl-2-trifluoromethyl-2H-1-benzopyran-3-carboxylic acid;

8-chloro-6-methyl-2-trifluoromethyl-2H-1-benzopyran-3-carboxylic acid;

8-chloro-6-methoxy-2-trifluoromethyl-2H-1-benzopyran-3-carboxylic acid;

6-bromo-8-chloro-2-trifluoromethyl-2H-1-benzopyran-3-carboxylic acid;

8-bromo-6-fluoro-2-trifluoromethyl-2H-1-benzopyran-3-carboxylic acid;

8-bromo-6-methyl-2-trifluoromethyl-2H-1-benzopyran-3-carboxylic acid;

8-bromo-5-fluoro-2-trifluoromethyl-2H-1-benzopyran-3-carboxylic acid;

6-chloro-8-fluoro-2-trifluoromethyl-2H-1-benzopyran-3-carboxylic acid;

6-bromo-8-methoxy-2-trifluoromethyl-2H-1-benzopyran-3-carboxylic acid;

6-[[(phenylmethyl)amino]sulfonyl]-2-trifluoromethyl-2H-1-benzopyran-3-carboxylic acid;

6-[(dimethylamino)sulfonyl]-2-trifluoromethyl-2H-1-benzopyran-3-carboxylic acid;

6-[(methylamino)sulfonyl]-2-trifluoromethyl-2H-1-benzopyran-3-carboxylic acid;

6-[(4-morpholino)sulfonyl]-2-trifluoromethyl-2H-1-benzopyran-3-carboxylic acid;

6-[(1,1-dimethylethyl)aminosulfonyl]-2-trifluoromethyl-2H-1-benzopyran-3-carboxylic acid;
6-[(2-methylpropyl)aminosulfonyl]-2-trifluoromethyl-2H-1-benzopyran-3-carboxylic acid;
6-methylsulfonyl-2-trifluoromethyl-2H-1-benzopyran-3-carboxylic acid;
8-chloro-6-[[(phenylmethyl)amino]sulfonyl]-2-trifluoromethyl-2H-1-benzopyran-3-carboxylic acid;
6-phenylacetyl-2-trifluoromethyl-2H-1-benzopyran-3-carboxylic acid;
6,8-dibromo-2-trifluoromethyl-2H-1-benzopyran-3-carboxylic acid;
8-chloro-5,6-dimethyl-2-trifluoromethyl-2H-1-benzopyran-3-carboxylic acid;
(S)-6,8-dichloro-2-trifluoromethyl-2H-1-benzopyran-3-carboxylic acid;
6-benzylsulfonyl-2-trifluoromethyl-2H-1-benzopyran-3-carboxylic acid;
6-[[N-(2-furylmethyl)amino]sulfonyl]-2-trifluoromethyl-2H-1-benzopyran-3-carboxylic acid;
6-[[N-(2-phenylethyl)amino]sulfonyl]-2-trifluoromethyl-2H-1-benzopyran-3-carboxylic acid;
6-iodo-2-trifluoromethyl-2H-1-benzopyran-3-carboxylic acid;
7-(1,1-dimethylethyl)-2-pentafluoroethyl-2H-1-benzopyran-3-carboxylic acid; and
6-chloro-2-trifluoromethyl-2H-1-benzothiopyran-3-carboxylic acid;
or a pharmaceutically acceptable salt thereof;
[4] A compound described in any of [1] to [3], wherein the compound of formula (I') is one or more selected from the group consisting of
6-chloro-8-methyl-2-trifluoromethyl-2H-1-benzothiopyran-3-carboxylic acid;
(S)-6-chloro-7-(1,1-dimethylethyl)-2-trifluoromethyl-2H-1-benzothiopyran-3-carboxylic acid;
(S)-6,8-dichloro-2-trifluoromethyl-2H-1-benzopyran-3-carboxylic acid; and
(S)-6-trifluoromethoxy-2-trifluoromethyl-2H-1-benzopyran-3-carboxylic acid;
or a pharmaceutically acceptable salt thereof;
[5] A compound described in any of [1] to [4], wherein X is O;
or a pharmaceutically acceptable salt thereof;
[6] A pharmaceutical composition for preventing or treating an ocular disease, wherein the pharmaceutical composition contains a compound as described in any one of [1] to [5] or a pharmaceutically acceptable salt thereof as an active ingredient;
[7] The pharmaceutical composition described in [6], wherein the ocular disease is retinochoroidal degeneration;
[8] The pharmaceutical composition described in [6] or [7], wherein the ocular disease is accompanied with retinochoroidal neovascularization;
[9] The pharmaceutical composition described in [6], wherein the ocular disease is one or more selected from the group consisting of age-related macular degeneration, retinopathy of prematurity, polypoidal choroidal vasculopathy, diabetic retinopathy, diabetic macular edema, ischemic proliferative retinopathy, retinitis pigmentosa, cone dystrophy, proliferative vitreoretinopathy, retinal artery occlusion, retinal vein occlusion, keratitis, conjunctivitis, uveitis, Leber's disease, retinal detachment, neovascular glaucoma, corneal neovascularization, retinochoroidal neovascularization and an ocular disease accompanied with the diseases thereof;

[10] A kit for preventing or treating an ocular disease, wherein the kit comprises a compound described in any one of [1] to [5] or a pharmaceutically acceptable salt thereof;
[11] A compound described in any one of [1] to [5] or a pharmaceutically acceptable salt thereof for preventing or treating an ocular disease, wherein the compound has a benzopyran ring or a naphtopyran ring;
[12] A use of a compound as described in any one of [1] to [5] or a pharmaceutically acceptable salt thereof for the manufacture of a medicament for preventing or treating an ocular disease;
[13] The use described in [12], wherein the ocular disease is retinochoroidal degeneration;
[14] The use described in [12], wherein the ocular disease is accompanied with retinochoroidal neovascularization;
[15] The use described in [12], wherein the ocular disease is one or more selected from the group consisting of age-related macular degeneration, retinopathy of prematurity, polypoidal choroidal vasculopathy, diabetic retinopathy, diabetic macular edema, ischemic proliferative retinopathy, retinitis pigmentosa, cone dystrophy, proliferative vitreoretinopathy, retinal artery occlusion, retinal vein occlusion, keratitis, conjunctivitis, uveitis, Leber's disease, retinal detachment, retinal pigment epithelial detachment, neovascular glaucoma, corneal neovascularization, retinochoroidal neovascularization and an ocular disease accompanied with the diseases thereof;
[16] A method for preventing or treating an ocular disease, wherein the method comprises administering an effective amount of a compound described in any one of [1] to [5] to patients;
[17] The method described in [16], wherein the ocular disease is retinochoroidal degeneration;
[18] The method in [16], wherein the ocular disease is accompanied with retinochoroidal neovascularization;
[19] The method described in [16], wherein the ocular disease is one or more selected from the group consisting of age-related macular degeneration, retinopathy of prematurity, polypoidal choroidal vasculopathy, diabetic retinopathy, diabetic macular edema, ischemic proliferative retinopathy, retinitis pigmentosa, cone dystrophy, proliferative vitreoretinopathy, retinal artery occlusion, retinal vein occlusion, keratitis, conjunctivitis, uveitis, Leber's disease, retinal detachment, retinal pigment epithelial detachment, neovascular glaucoma, corneal neovascularization, retinochoroidal neovascularization and an ocular disease accompanied with the diseases thereof; and
[20] A compound as defined by the following formula (I) for use in preventing or treating an ocular disease in animal including human:

{Chem. 2}

(I)

wherein
X is selected from O, S and $NR^a$;
$R^a$ is selected from hydrido, $C_1$-$C_3$-alkyl, (optionally substituted phenyl)-methyl, and phenylmethyl; wherein the phenyl ring is substituted by 1 to 3 substituents independently selected from $C_1$-$C_6$-alkyl, hydroxyl, halo, $C_1$-$C_6$-haloalkyl, nitro, cyano, $C_1$-$C_6$-alkoxy and $C_1$-$C_6$-alkylamino;

R is carboxyl;

R" is selected from hydrido and $C_2$-$C_6$-alkenyl;

$R^1$ is selected from $C_1$-$C_3$-perfluoroalky, chloro, $C_1$-$C_6$-alkylthio, nitro, cyano and cyano-$C_1$-$C_3$-alkyl;

$R^2$ is one or more radicals independently selected from hydrido; halo; $C_1$-$C_6$-alkyl; $C_2$-$C_6$-alkenyl; $C_2$-$C_6$-alkynyl; halo-$C_2$-$C_6$-alkynyl; pheny-$C_1$-$C_6$-alkyl; phenyl-$C_2$-$C_6$-alkynyl; phenyl-$C_2$-$C_6$-alkenyl; $C_1$-$C_3$-alkoxy; methylenedioxy; $C_1$-$C_3$-alkoxy-$C_1$-$C_3$-alkyl; $C_1$-$C_3$-alkylthio; $C_1$-$C_3$-alkylsulfinyl; phenyloxy; phenylthio; phenylsulfinyl; $C_1$-$C_3$-haloalkyl-$C_1$-$C_3$-hydroxyalkyl; phenyl-$C_1$-$C_3$-alkoxy-$C_1$-$C_3$-alkyl; $C_1$-$C_3$-haloalkyl; $C_1$-$C_3$-haloalkoxy; $C_1$-$C_3$-haloalkylthio; $C_1$-$C_3$-hydroxyalkyl; hydroxyimino-$C_1$-$C_3$-alkyl; $C_1$-$C_6$-alkylamino; nitro; cyano; amino; aminosulfonyl; N—($C_1$-$C_6$-alkyl)aminosulfonyl; N-arylaminosulfonyl; N-heteroarylaminosulfonyl; N-(phenyl-$C_1$-$C_6$-alkyl)aminosulfonyl; N-(heteroaryl-$C_1$-$C_6$-alkyl)aminosulfonyl; phenyl-$C_1$-$C_3$-alkylsulfonyl; 5- to 8-membered heterocyclylsulfonyl; $C_1$-$C_6$-alkylsulfonyl; phenyl; optionally substituted phenyl substituted by one or more radials selected from chloro, fluoro, bromo, methoxy, methylthio and methylsulfonyl; 5- to 9-membered heteroaryl; chloro substituted thienyl; phenyl-$C_1$-$C_6$-alkylcarbonyl; phenylcarbonyl; 4-chlorophenylcarbonyl; 4-hydroxyphenylcarbonyl; 4-trifluoromethylphenylcarbonyl; 4-methoxyphenylcarbonyl; aminocarbonyl; formyl; and $C_1$-$C_6$-alkylcarbonyl;

the A ring atoms $A^1$, $A^2$, and $A^3$ are carbon and $A^4$ is carbon or nitrogen;

or $R^2$ together with ring A forms a naphthyl, benzofurylphenyl, or quinolyl radical;

or a pharmaceutically acceptable salt thereof.

Effect of the Invention

As mentioned above, a lot of COX-2 inhibitors are known, but the third generation COX-2 inhibitors of the present invention, compared to conventional COX-2 inhibitors, show an excellent effect against a chorioretinal neovascularization inhibitory activity. Namely, in evaluation studies of inhibitory activities against a chorioretinal neovascularization, a compound of the present invention completely inhibits events accompanied with a chorioretinal neovascularization to control levels. Therefore, it is particularly useful for preventing or treating an ocular disease accompanied with neovascularization.

More specifically, a compound of the present invention is useful as a prophylactic and/or therapeutic agent for age-related macular degeneration, retinopathy of prematurity, polypoidal choroidal vasculopathy, diabetic retinopathy, diabetic macular edema, ischemic proliferative retinopathy, retinitis pigmentosa, cone dystrophy, proliferative vitreoretinopathy, retinal artery occlusion, retinal vein occlusion, keratitis, conjunctivitis, uveitis, Leber's disease, retinal detachment, retinal pigment epithelial detachment, neovascular glaucoma, corneal neovascularization, retinochoroidal neovascularization and an ocular disease accompanied with the diseases thereof. In addition, a compound of the present invention is useful for providing a pharmaceutical composition for preventing or treating the said diseases.

DESCRIPTION OF EMBODIMENTS

Hereafter, definitions of terms and phrases (atoms, groups, rings, etc.) to be used in the present specification will be described in detail. Further, when the other definitions of terms and phrases are applied to the definitions of terms and phrases mentioned below, preferred ranges of the respective definitions and the like can also be applied.

As used in compounds represented by the formula (I) or the formula (I'), the term "alkyl" as a group or part of a group e.g. alkoxy or hydroxyalkyl refers to a straight or branched alkyl group in all isomeric forms.

The term "$C_1$-$C_6$ alkyl" refers to an alkyl group, as represented by the formula (I) or the formula (I'), containing at least 1, and at most 6 carbon atoms. Examples of such alkyl groups include methyl, ethyl, propyl, isopropyl, n-butyl, isobutyl, sec-butyl, tert-butyl and the like.

The term "$C_2$-$C_6$ alkenyl" refers to an alkenyl group, as represented by the formula (I) or the formula (I'), containing at least 2, and at most 6 carbon atoms. Examples of such alkenyl groups include vinyl, 1-propenyl, allyl, 1-butenyl, 2-butenyl, 3-butenyl, pentenyl, hexenyl and the like.

The term "$C_2$-$C_6$ alkynyl", refers to an alkynyl group, as represented by the formula (I) or the formula (I'), containing at least 2, and at most 6 carbon atoms. Examples of such alkynyl groups include ethynyl, 1-propynyl, 2-propynyl, 1-butynyl, 3-butynyl, pentynyl, hexynyl and the like.

In a compound represented by the formula (I) or the formula (I'), the term "halogen" refers to fluorine (F), chlorine (Cl), bromine (Br), or iodine (I) and the term "halo" refers to the halogen: fluoro (—F), chloro (—Cl), bromo (—Br) and iodo (—I).

As the term "heteroring" in a heteroaryl, 5- to 8-membered heterocyclyl and 5- to 9-membered heteroaryl in the definition of the formula (I) or the formula (I'), 5- to 6-membered heteroring containing one to three selected from O, N, and S, exemplified by furyl, thienyl, pyridyl, thiazolyl and the like are preferable. These groups may be substituted with conventional substituents such as $C_1$-$C_6$ lower alkyl group, hydroxyl group, amino group, carboxyl group, and halogen. Also, 5- to 8-membered heterocyclyl ring and 5- to 9-membered heteroaryl may be a bicyclic group such as benzimidazolyl.

In a compound represented by the formula (I) or the formula (I'), the term "$C_1$-$C_6$ alkoxy" refers to an alkoxy group containing at least 1, and at most 6 carbon atoms. Examples of such alkoxy groups include methoxy group, ethoxy group, normal propoxy group, isopropoxy group, normal butoxy group, secondary butoxy group, tertiary butoxy group, normal pentyl group, isopentyl group, tertiary pentyl group, neopentyl group, 2,3-dimethylpropyl group, 1-ethylpropyl group, 1-methylbutyloxy group, normal hexyloxy group, isohexyloxy group, 1,1,2-trimethylpropyloxy group and the like;

the term "$C_1$-$C_6$ alkylthio" refers to an alkylthio group containing at least 1, and at most 6 carbon atoms. Examples of such alkylthio groups include methylthio group, ethylthio group, normal propylthio group, isopropylthio group, normal butylthio group, secondary butylthio group, tertiary butylthio group, normal pentylthio group, isopentylthio group, tertiary pentylthio group, neopentylthio group, 2,3-dimethylpropylthio group, 1-ethylpropylthio group, 1-methylbutylthio group, normal hexylthio group, isohexylthio group, 1,1,2-trimethylpropylthio group and the like;

the term "$C_1$-$C_3$ alkylsulfinyl" refers to an alkylsulfinyl group containing at least 1, and at most 6 carbon atoms. Examples of such alkylsulfinyl groups include methylsulfinyl group, ethylsulfinyl group, normal propylsulfinyl group, isopropylsulfinyl group and the like;

the term "$C_1$-$C_6$ alkylsulfonyl" refers to an alkylsulfonyl group containing at least 1, and at most 6 carbon atoms. Examples of such alkylsulfonyl groups include methylsulfonyl group, ethylsulfonyl group, normal propylsulfonyl group, isopropylsulfonyl group, normal butylsulfonyl group, secondary butylsulfonyl group, tertiary butylsulfonyl group, normal pentylsulfonyl group, isopentylsulfonyl group, tertiary pentylsulfonyl group, neopentylsulfonyl group, 2,3-dimethylpropylsulfonyl group, 1-ethylpropylsulfonyl group, 1-methylbutylsulfonyl group, normal hexylsulfonyl group, isohexylsulfonyl group, 1,1,2-trimethylpropylsulfonyl group and the like;

the term "$C_1$-$C_6$ alkylcarbonyl" refers to an alkylcarbonyl group containing at least 1, and at most 6 carbon atoms. Examples of such alkylcarbonyl groups include acetyl group, propanoyl group, butanoyl group, 2-methyl-propanoyl group, pentanoyl group, 2-methylbutanoyl group, 3-methylbutanoyl group and the like; and the term "$C_1$-$C_6$ alkylamino" refers to an alkylamino group containing at least 1, and at most 6 carbon atoms. Examples of such alkylamino groups include methylamino group, ethylamino group, propylamino group, isopropylamino group, dimethylamino group, diethylamino group, ethylmethylamino group, dipropylamino group, methylpropylamino group, diisopropylamino group and the like.

For example, the third generation coxib compound represented by formula (I) or formula (I') is described in Patent Document 1 (Japanese Patent No. 4577534) and the like. A compound of formula (I) or formula (I') or a salt thereof can be easily prepared by known methods or known methods per se.

The term "ocular disease" in the present invention refers to, but not limited to, such ocular diseases accompanied with chorioretinal degenerative disease or neovascularization.

The chorioretinal is an organization combined retina and choroid.

Examples of an ocular disease accompanied with ocular neovascularization may include, but not limited to, age-related macular degeneration or the like, and therefore, a compound of the present invention is useful as a prophylactic and/or therapeutic agent for age-related macular degeneration, retinopathy of prematurity, polypoidal choroidal vasculopathy, diabetic retinopathy, diabetic macular edema, ischemic proliferative retinopathy, retinitis pigmentosa, cone dystrophy, proliferative vitreoretinopathy, retinal artery occlusion, retinal vein occlusion, keratitis, conjunctivitis, uveitis, Leber's disease, retinal detachment, retinal pigment epithelial detachment, neovascular glaucoma, corneal neovascularization, retinochoroidal neovascularization and an ocular disease accompanied with the diseases thereof.

The specific diseases are for a better understanding of the invention and are not intended to limit the scope of the invention.

In terms of pharmaceutically acceptable salts of the compound represented by the formula (I) or the formula (I'), the nature of the salt is not critical, provided that it is pharmaceutically acceptable. Pharmaceutically-acceptable acid addition salts of the compound represented in the formula (I) or the formula (I') can be prepared from a suitable inorganic acid or from a suitable organic acid. Examples of such inorganic acids are hydrochloric, hydrobromic, hydroiodic, nitric, carbonic, sulfuric and phosphoric acid. Examples of such organic acids are selected from aliphatic, cycloaliphatic, aromatic, araliphatic, heterocyclic, carboxylic and sulfonic classes of organic acids, which are exemplified by formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, 4-hydroxybenzoic, phenylacetic, mandelic, embonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric, and galacturonic acid. Suitable pharmaceutically-acceptable base addition salts of the compounds represented by the formula (I) or the formula (I') include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethylpiperidine, histidine, glucamine, isopropylamine, lysine, morpholine, N-ethylmorpholine, piperazine, piperidine, triethylamine, and trimethylamine. All salts described above can be prepared from the compound represented by the formula (I) or the formula (I') and a suitable acid or a suitable base by conventional methods. Then an esterified carboxyl group preferably includes a group capable of converting to a carboxyl group by hydrolysis in vivo (e.g., t-butoxycarbonyl group). Since such groups which can easily converting to a carboxyl group by hydrolysis in vivo are conventionally well established, the present invention may make in accordance with such established known techniques in terms of the type, manufacturing, and the like.

Compounds of the present invention containing one or more asymmetric carbon atoms can exist as two or more stereoisomers. Where a compound of the present invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of the present invention, including compounds exhibiting more than/equal to two type of isomerism, and mixtures of one or more thereof. Also included are acid addition salts or base salts wherein the counter ion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor and resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the present invention contains an acidic or basic moiety, an acid or base such as tartaric acid or 1-phenylethylamine. The resulting diastereomeric mixture may be separated by chromatography and/or fractional crystallization and one or both of the diastereoisomers can be converted to the corresponding pure enantiomer(s) by means well known to a skilled person.

Chiral compounds of the present invention (and chiral precursors thereof) may be obtained in enantiomerically-enriched form using chromatography, typically HPLC, on an asymmetric resin with a mobile phase containing alcohol from 0 to 50 (w/w) %, typically ethanol and 2-propanol from 2 to 20 (w/w) %, and carboxylic acid from 0 to 5 (w/w) %, typically hydrocarbon including acetic acid from 0.1 to 0.5 (w/w) %, typically heptane or hexane. Concentration of the eluate affords the enriched mixture.

More specifically, heptane/2-propanol/trifluoroacetic acid (95/5/0.1), heptane/2-propanol/acetic acid (90/10/0.1), heptane/2-propanol/acetate (90/10/0.5), heptane/ethanol/acetic acid (95/5/0.1) or the like may be used for the said mobile phase.

Stereoisomeric conglomerates may be separated by conventional techniques known to those skilled in the art—see, for example, Stereochemistry of Organic Compounds by E L Eliel (Wiley, New York, 1994).

The present invention includes all pharmaceutically acceptable isotopically-labeled compounds of the present invention wherein one or more atoms are replaced by atoms having the same atomic number, but an atomic mass or mass number different from the atomic mass or mass number usually found in nature.

Examples of isotopes suitable for inclusion in the compounds of the present invention include isotopes of hydrogen such as $^2H$ and $^3H$, carbon such as $^{11}C$, $^{13}C$ and $^{14}C$, chlorine such as $^{38}Cl$, fluorine such as $^{18}F$, iodine such as $^{123}I$ and $^{125}I$, nitrogen such as $^{13}N$ and $^{15}N$, oxygen such as $^{15}O$, $^{17}O$ and $^{18}O$, phosphorus such as $^{32}P$, and sulfur such as $^{35}S$.

Certain isotopically-labeled compounds of the present invention, for example, those incorporating a radioactive isotope, are useful in drug and/or substrate tissue distribution studies associated with cancer therapy which includes diagnosis, alleviation of symptoms, improvement of QOL, and prophylaxis. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the present invention include those wherein the solvent for crystallization may be isotopically substituted, e.g., $D_2O$, $d_6$-acetone, and $d_6$-DMSO.

Compounds of the present invention intended for pharmaceutical use may be administered as crystalline or amorphous products. They may be obtained, for example, as solid plugs, powders, or films by methods such as precipitation, crystallization, freeze drying, spray drying, and evaporative drying. Microwave or radio frequency drying may be used for this purpose.

A compound of the present invention exhibits an excellent effect on HUVEC (Human Umbilical Vein Endothelial Cells) lumen formation study, VEGF (vascular endothelial growth factor)-induced human retinal microvascular endothelial cell (HRMEC) proliferation study, and VEGF-induced HRMEC migration study as in vivo evaluation studies of inhibitory activities against retinal neovascularization.

In a mouse model of choroidal neovascularization induced by krypton laser irradiation and a model of hyperoxia-induced retinal neovascularization as in vivo studies, a compound of the present invention exhibits an excellent inhibitory effect on choroidal neovascularization through intravitreal administration.

Incidentally, this model is considered to be a model of an ocular inflammatory disease and/or a model of a retinal disease typified by age-related macular degeneration or the like, and therefore, a compound of the present invention is useful as a prophylactic and/or therapeutic agent for age-related macular degeneration, retinopathy of prematurity, polypoidal choroidal vasculopathy, diabetic retinopathy, diabetic macular edema, ischemic proliferative retinopathy, retinitis pigmentosa, cone dystrophy, proliferative vitreoretinopathy, retinal artery occlusion, retinal vein occlusion, keratitis, conjunctivitis, uveitis, Leber's disease, retinal detachment, retinal pigment epithelial detachment, neovascular glaucoma, corneal neovascularization, retinochoroidal neovascularization and an ocular disease accompanied with the diseases thereof.

The present compound can be administered orally or parenterally. Examples of the mode of administration include oral administration, ophthalmic topical administration (such as eye drop administration, instillation in the conjunctivalsac, intravitreal administration, subconjunctival administration and sub-Tenon's administration), intravenous administration and transdermal administration, and the present compound can be formulated into a preparation suitable for such an administration mode by properly selecting and using a pharmaceutically acceptable additive as needed.

Examples of the dosage form include, in the case of an oral preparation, a tablet, a capsule, a granule and a powder, and, in the case of a parenteral preparation, an injection, an eye drop, an eye ointment, an insert and an intraocular implant.

For example, in the case of a tablet, a capsule, a granule, a powder or the like, such a preparation can be prepared by properly selecting and using an excipient such as lactose, glucose, D-mannitol, anhydrous calcium hydrogen phosphate, starch or sucrose; a disintegrant such as carboxymethyl cellulose, calcium carboxymethyl cellulose, croscarmellose sodium, crosspovidone, starch, partially gelatinized starch or low-substituted hydroxypropyl cellulose; a binder such as hydroxypropyl cellulose, ethyl cellulose, gum arabic, starch, partially gelatinized starch, polyvinylpyrrolidone or polyvinyl alcohol; a lubricant such as magnesium stearate, calcium stearate, talc, hydrous silicon dioxide or a hydrogenated oil; a coating agent such as purified sucrose, hydroxypropylmethyl cellulose, hydroxypropyl cellulose, methyl cellulose, ethyl cellulose or polyvinylpyrrolidone; a corrigent such as citric acid, aspartame, ascorbic acid or menthol; or the like as needed.

An injection can be prepared by properly selecting and using a tonicity agent such as sodium chloride; a buffer such as sodium phosphate; a surfactant such as polyoxyethylene sorbitan monooleate; a viscosity-increasing agent such as methyl cellulose; or the like as needed.

An eye drop can be prepared by properly selecting and using a tonicity agent such as sodium chloride or concentrated glycerin; a buffer such as sodium phosphate or sodium acetate; a surfactant such as polyoxyethylene sorbitan monooleate, polyoxyl 40 stearate or polyoxyethylene hydrogenated castor oil; a stabilizer such as sodium citrate or sodium edetate; a preservative such as benzalkonium chloride or paraben; or the like as needed. The pH of the eye drop is permitted as long as it falls within the range that is acceptable as an ophthalmic preparation, but is preferably in the range of from 4 to 8, and more preferably in the range of from 5 to 7. As a pH adjusting agent, a normal pH adjusting agent, for example, sodium hydroxide and/or hydrochloric acid may be used.

The material of the resinous container consists essentially of polyethylene. The container material may contain minor amounts of other materials than polyethylene, for example polypropylene, polyethylene terephthalate, polyvinyl chloride, acrylic resins, polystyrene, polymethyl methacrylate and nylon 6. The amount of said materials is preferably no more than about 5 to 10% of the total container material. Polyethylene is classified to several types by the density thereof, namely low density polyethylene (LDPE), middle density polyethylene (MDPE), high density polyethylene (HDPE), etc and these polyethylenes are included in this invention. Preferable polyethylene is LDPE.

Containers for packaging and storing the aqueous ophthalmic solution according to the invention include all container forms suitable for user-friendly topical ophthalmic delivery. Consequently, the containers may be selected for example from the group consisting of bottles, tubes, ampoules, pipettes and fluid dispensers, in single unit dose form or in multidose form. According to a preferred embodiment of the invention, the aqueous ophthalmic solution is in a single dose or unit dose form.

The containers for the ophthalmic solution according to the invention are preferably manufactured by extrusion blow moulding method. Extrusion blow moulding gives smoother inner surface of the container compared to injection blow moulding, which is commonly used to manufacture for example polyethylene multidose bottles. The smoother inner surface gives better chemical stability of prostaglandins in the polyethylene container compared to polyethylene container manufactured by injection blow moulding. Furthermore, when single-dose containers are used, they are sterilized during the moulding process by heat and no additional sterilization of containers is needed, which also improves stability of prostaglandins in a single-dose container (see EP 1 825 855 and EP 1 349 580). In general, a unit dose ophthalmic container manufactured by blow moulding method has a volume of about 1 ml and about 0.2 to 0.5 ml of solution is filled. A large variety of shapes are known in such containers. Typical examples are seen in U.S. Pat. No. 5,409,125 and U.S. Pat. No. 6,241,124.

Although unit dose containers are preferred for the purposes of the invention, the aqueous ophthalmic solution according to the invention remains soluble, stable and bioavailable also in fluid dispensers for dispensing of minute amounts of germ-free fluid or in any other container-type wherein the aqueous ophthalmic solution is in contact with container material consisting essentially of polyethylene. Such fluid dispensers are disclosed for example in U.S. Pat. No. 5,614,172.

The preservative-free aqueous ophthalmic solution according to the invention can be stored at room temperature in the above mentioned suitable containers, including unit dose pipettes and dispensers.

A preferred embodiment according to the invention is an aqueous ophthalmic solution for treating ocular hypertension and glaucoma, which comprises 0.0001-0.01% w/v of a compound of formula (I) or formula (I'), or a pharmaceutically acceptable salt thereof as an active ingredient;
0.05-0.5% w/v non-ionic surfactant;
0.005-0.2% w/v stabilizing agent;
substantially no preservatives, and optionally buffering agents, pH adjusters and tonicity agents conventionally used in ophthalmic solutions, in a container consisting essentially of polyethylene.

An eye ointment can be prepared using a widely used base such as white petrolatum or liquid paraffin.

An insert can be prepared using a biodegradable polymer such as hydroxypropyl cellulose, hydroxypropylmethyl cellulose, a carboxy vinyl polymer or polyacrylic acid, and if necessary, an excipient, a binder, a stabilizer, a pH adjusting agent or the like can be properly selected and used as appropriate.

A preparation for intraocular implant can be prepared using a biodegradable polymer such as polylactic acid, polyglycolic acid, a lactic acid-glycolic acid copolymer or hydroxypropyl cellulose, and if necessary, an excipient, a binder, a stabilizer, a pH adjusting agent or the like can be properly selected and used as appropriate.

The dose of the present compound can be properly selected depending on the dosage form, symptoms, age, body weight of a patient or the like. For example, in the case of oral administration, it can be administered in an amount of from 0.01 to 5000 mg, preferably from 0.1 to 2500 mg, particularly preferably from 0.5 to 1000 mg per day in a single dose or several divided doses. In the case of an injection, it can be administered in an amount of from 0.00001 to 2000 mg, preferably from 0.0001 to 1500 mg, particularly preferably from 0.001 to 500 mg per day in a single dose or several divided doses. In the case of an eye drop, a preparation containing the present compound at a concentration of from 0.00001 to 10% (w/v), preferably from 0.0001 to 5% (w/v), particularly preferably from 0.001 to 1% (w/v) can be instilled into the eye once or several times a day. In the case of an eye ointment, a preparation containing the present compound in an amount of from 0.0001 to 2000 mg can be applied. In the case of an insert or a preparation for intraocular implant, a preparation containing the present compound in an amount of from 0.0001 to 2000 mg can be inserted or implanted.

The present invention also relates to combining separate pharmaceutical compositions in kit form. The kit comprises a container for containing the separate compositions such as a divided bottle or a divided foil packet, however, the separate compositions may also be contained within a single, undivided container. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

A kit product, prefilled syringe, which comes prefilled with desired medicament in a syringe container, can be provided.

EXAMPLE

The present invention is explained in more detail in the following by referring to Reference Examples and Examples, which are not to be construed as limitative but just typical examples.

A compound of formula (I) or formula (I') can be prepared using any method known in the art (for example, patent literature 1, JP Patent No. P4577534).

Examples of an ocular disease model accompanied with neovascularization include the following studies.
Evaluation Studies of Inhibitory Activities Against Neovascularization
HUVEC Tube Formation Study In co-culture system of human fibroblasts and human umbilical vein endothelial cells (HUVEC), the effect of the drug on the promotion of the HUVEC tube formation by adding VEGF-A is studied. A drug to be evaluated is added to the VEGF-A-added medium. The cultured cells are immobilized after a certain period of time, and the HUVEC stained with an anti-CD31 antibody is subject to morphological observation, and then tube area, total length of tube network, number of branch points, number of branch and the like are evaluated. Journal of Pharmacological Sciences, 129, 451-456 (2007).
VEGF-Induced Human Retinal Microvascular Endothelial Cells (HRMEC) Proliferation Study VEGF is a factor which promotes neovascularization and is thought to be one of the causes of development or progression of age-related macular degeneration (Prog. Retinal Eye Res., 22 (1), 1-29 (2003)). Therefore, the inhibitory effect of the compounds of the invention against VEGF-induced cell proliferation is assessed by using human retinal vascular endothelial cells (HRMEC).

HRMEC are seeded in 96-well plates at $2.0 \times 10^3$ cells/well, and is cultured under the conditions of 5% $CO_2$/95% air for 24 hours. Then the culture medium is exchanged with CSC medium containing 10% fetal bovine serum and the cells are cultured for 24 hours. The culture broth is exchanged with vehicle medium or study medium containing the compound of the invention at 0.1, 1.0, 10, or 100 microM. After preincubation for 1 hour, VEGF-A solution is added to be a concentration of 10 ng/ml, and the cells cultured for 24 hours. The culture broth without adding VEGF-A solution is also treated in the same manner. Then to the culture broth is added CCK-8, and the cells are cultured for 3 hours, then the absorbance (OD492) is measured.

In accordance with the following formula, the cell proliferation inhibition rate (%) of each compound-treated group is calculated. The number of examples of each group is six.

$$\text{Cell proliferation inhibition rate (\%)} = ((B_X - B_N)/(B_O - B_N)) \times 100 \quad \text{[equation]}$$

Figure 1:
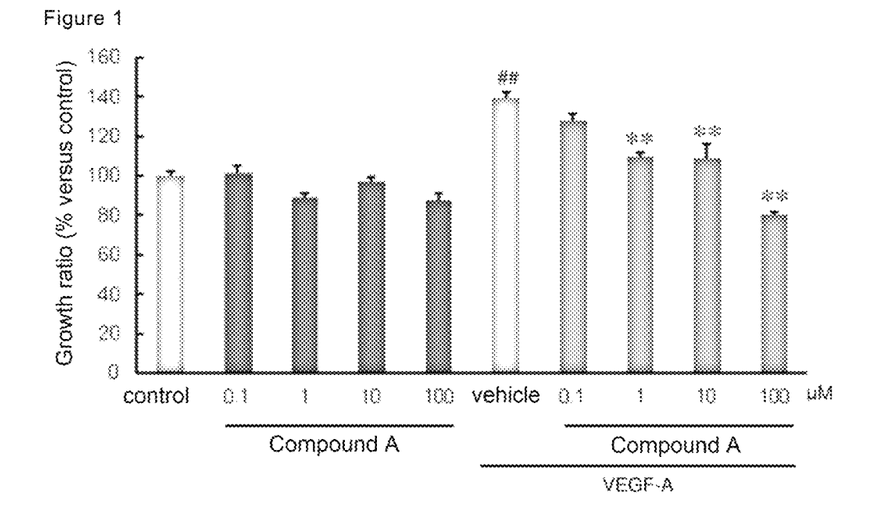
FIG. 1 shows mean and standard error in evaluation studies of inhibitory activities against retinal neovascularization wherein Compound A is (S)-6-chloro-7-(1,1-dimethylethyl)-2-trifluoromethyl-2H-1-benzopyran-3-carboxylic acid (n=6). ##:P<0.01, **:P<0.01 (Compound A vs. vehicle in Dunnet's test).

$B_O$: absorbance of vehicle-treated group
$B_X$: absorbance of compound-treated group
$B_N$: absorbance of non-treated group The result of Compound A is shown in FIG. 1. Although addition of Compound A alone has no effect on the proliferation of HRMEC (on the left side in FIG. 1), a compound of the invention inhibits the proliferation of HRMEC induced by VEGF-A in a dose-dependent manner (on the right side in FIG. 1). Compound A inhibits the cell proliferation to control levels at 10 to 100 microM.
VEGF-Induced Human Retinal Microvascular Endothelial Cells (HRMEC) Migration Study The effects of the drug on the migration of human retinal microvascular endothelial cells (HRMEC) are studied.

HRMEC are seeded in a 12-well plate coated with collagen at a density of $4 \times 10^4$ cells/well, and is cultured at 37° C. under 5% $CO_2$ for 48 hours. Then after the medium is exchanged with the medium without the growth factors, the cells are cultured for 24 hours. Then, the cells present on the center line of the well scratched by using a 1 mL tip, and medium is exchanged by washing the well with PBS (phosphate buffer solution). Immediately after that, image of HRMEC is recorded by using a CCD camera (pre-migration). VEGF-A and a compound of the present invention are added to the well to attain the target concentration, and the cells are incubated for 24 hours. After migration, each well is recorded in a similar manner, and the number of cells migrated to the place where the cells are scratched is measured comparing with that before migration.

By addition of VEGF-A, the number of migrated cell of HRMEC increased compared with that of the control group. A significant inhibitory effect on the migration of VEGF-induced HRMEC by addition of the compound of the present invention is observed.
Laser-Induced Choroidal Neovascularization (CNV) Model A male C57BL/6J mouse is used. Mydrin P ophthalmic solution (registered trademark, Santen Pharmaceutical) is instilled into the right eye of the mouse to cause mydriasis. Animals are anesthetized, and laser irradiation is performed on around the circumference of the optic disk with eight equally space using a laser photocoagulation apparatus.

After photocoagulation, intravitreal administration of drugs to the right eye (administering 2 microL of a solution of 60 microM and 600 microM using a solvent obtained by mixing 0.1N NaOH and pH 7.2 PBS containing $1.5 \times 10^{-3}$N HCl, at the ratio of 16:84) or oral administration/subcutaneous administration/intraperitoneal administration is conducted. After instillation of Cravit (registered trademark, Daiichi Sankyo) ophthalmic solution 0.5% into the right eye, the ocular fundus photography is promptly performed using an ocular fundus camera. On day 7 and day 14 after laser radiation, 10-fold diluted Fluorescite (registered trademark, Nippon Alcon) Intravenus Injection is injected into the tail vein of the anesthetized animal, and the ocular fluorescein fundus angiography is promptly performed using an ocular fundus camera.

On day 15 after after laser radiation, fluorescein-conjugated dextran (FITC-dextran) is injected into the tail vein of the anesthetized animal. After securing the eyeball excised from the animals, fixed, and a choroidal flat mount specimen is prepared under the microscope. Choroidal flat mounts specimens are observed using a confocal laser scanning microscope, and the CNV area of the image is calculated using the analysis software OLYMPUS FLUOVIEW FV1000.

Figure 2:
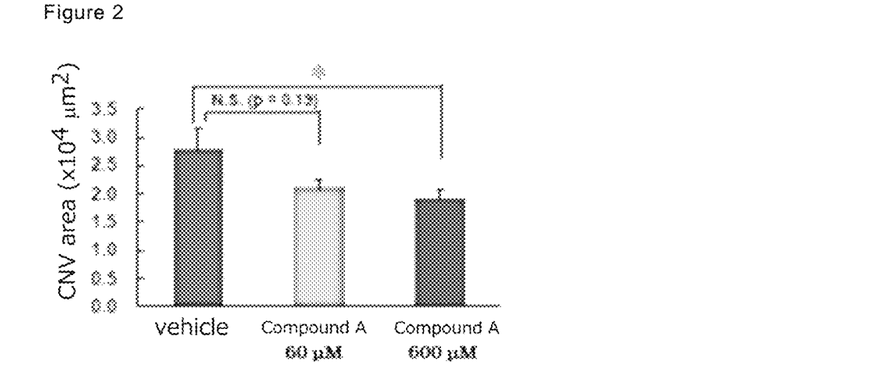
FIG. 2 shows mean and standard error in evaluation studies of inhibitory activities against retinal neovascularization wherein Compound A is (S)-6-chloro-7-(1,1-dimethylethyl)-2-trifluoromethyl-2H-1-benzopyran-3-carboxylic acid (n=7-11). N.S. means no significant difference. *:P<0.05 (Compound A vs. solvent in Dunnet's test).

The result of Compound A is shown in FIG. 2. CNV area is significantly reduced in comparison to the vehicle-treated group.

Figure 3:
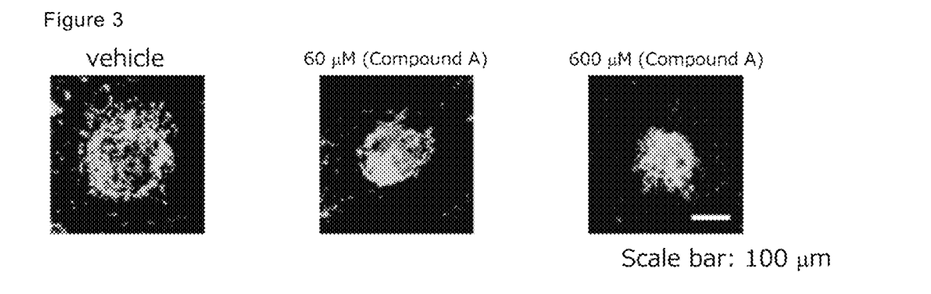
FIG. 3 shows images of histpathological specimens.

The pathological image of Compound A is shown in FIG. 3. CNV area is significantly reduced in comparison to the vehicle-treated group.

Hyperoxia-Induced Retinal Neovascularization (Oxygen-Induced Retinopathy: OIR) Model Experiments are carried out according to the method described in Journal of Pharmacological Sciences, 129, 451-456 (2007) and Invest Ophthamol Vis Sci. 1994; 35; p. 101-111. C57BL/6J mice are used. Hyperoxia-induced mouse model is carried out according to Smith's method (Smith L E et al., Invest Ophthamol Vis Sci. 1994; 35; p. 101-111). Newborn mouse is housed along with the parent mouse in high oxygen (75% $O_2$) in the cage, which is controlled by the oxygen control device from postnatal day 7 to postnatal day 12. On postnatal day 12, newborn mouse is back to atmospheric pressure conditions (21% $O_2$), and intravitreal administration of drugs to the right eye (administering 2 microL of a solution of 60 microM and 600 microM using a solvent obtained by mixing 0.1N NaOH and pH 7.2 PBS containing $1.5 \times 10^{-3}$N HCl, at the ratio of 16:84) or oral administration/subcutaneous administration/intraperitoneal administration is conducted and is housed up to postnatal day 17. Mice are anesthetized in the evaluation period, and FITC-dextran is administered from the left ventricle. After securing the eyeball excised from the animals, fixed, and a choroidal flat mount specimen is prepared under the microscope. Choroidal flat mount specimens are observed using a confocal laser scanning microscope, and the CNV area of the image is calculated using the analysis software OLYMPUS FLUOVIEW FV1000.

CNV area is significantly reduced by administering a compound of the present invention in comparison to the vehicle-treated group.

The invention claimed is:

1. A method for treating an ocular disease, comprising administering an effective amount of (S)-6-chloro-7-(1,1-dimethylethyl)-2-trifluoromethyl-2H-1-benzopyran-3-carboxylic acid or a pharmaceutically acceptable salt thereof to a patient, wherein the ocular disease is retinochoroidal degeneration.

2. A method for treating an ocular disease, comprising administering an effective amount of (S)-6-chloro-7-(1,1-dimethylethyl)-2-trifluoromethyl-2H-1-benzopyran-3-carboxylic acid or a pharmaceutically acceptable salt thereof to a patient, wherein the ocular disease is ocular disease accompanied with retinochoroidal neovascularization.

3. A method for treating an ocular disease, comprising administering an effective amount of (S)-6-chloro-7-(1,1-dimethylethyl)-2-trifluoromethyl-2H-1-benzopyran-3-carboxylic acid or a pharmaceutically acceptable salt thereof to a patient, wherein the ocular disease is ocular disease accompanied with neovascularization.

4. The method of claim 3, wherein the ocular disease accompanied with neovascularization is at least one selected from the group consisting of age-related macular degeneration, retinopathy of prematurity, polypoidal choroidal vasculopathy, ischemic proliferative retinopathy, retinitis pigmentosa, cone dystrophy, proliferative vitreoretinopathy, retinal artery occlusion, retinal vein occlusion, keratitis, conjunctivitis, uveitis, Leber's disease, retinal detachment, retinal pigment epithelial detachment, neovascular glaucoma, corneal neovascularization, retinochoroidal neovascularization and an ocular disease accompanied with the diseases.

* * * * *